United States Patent [19]

McKenzie et al.

[11] 4,221,714

[45] Sep. 9, 1980

[54] 11-(1,2,3,6-TETRAHYDRO-SUBSTITUTED-4-PYRIDYL)-DIBENZ[b,f][1,4]OXAZEPINES

[75] Inventors: Thomas C. McKenzie; John J. Brown, both of Pearl River, N.Y.

[73] Assignee: American Cyanamid Company, Stamford, Conn.

[21] Appl. No.: 63,481

[22] Filed: Aug. 3, 1979

[51] Int. Cl.² ............................................ C07D 413/02
[52] U.S. Cl. .............................. 260/244.4; 568/585; 546/298; 424/263
[58] Field of Search ..................... 546/270; 260/244.4

[56] References Cited

PUBLICATIONS

Chemical Abstracts, vol. 79, abst. 18780v, (1973).

Primary Examiner—John D. Randolph
Attorney, Agent, or Firm—Thomas M. Saunders

[57] ABSTRACT

Unsubstituted, mono-, di- or trisubstituted-11-(1,2,3,6-tetrahydro-substituted-4-pyridyl)-dibenz[b,f][1,4]oxazepines, useful as anti-psychotic agents..

8 Claims, No Drawings

11-(1,2,3,6-TETRAHYDRO-SUBSTITUTED-4-PYRIDYL)-DIBENZ[b,f][1,4]OXAZEPINES

PRIOR ART

The reduction of pyridinium salts is well known and is reviewed by Robert E. Lyle and Paul S. Anderson in *Advances in Heterocyclic Chemistry*, Vol. 6, A. R. Katritzky and A. J. Boulton editors, Academic Press, New York, 1966, p. 45. The synthesis and CNS utility of 11-piperidyl-dibenz[b,f][1,4]oxazepines was disclosed by Charles Frederick Howell, Paul Raminez, and Robert Allis Hardy, Jr., in U.S. Pat. No. 3,501,483, issued Mar. 17, 1970.

SUMMARY OF THE INVENTION

This invention is concerned with compounds of the formula:

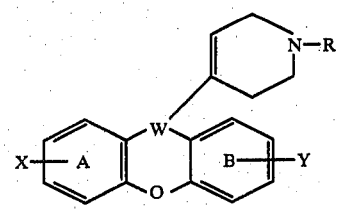

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; R is selected from the group consisting of lower alkyl ($C_1$-$C_6$) and hydroxy lower alkyl; W is selected from the group consisting of

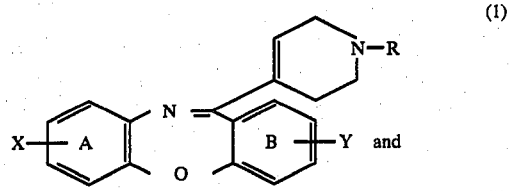

and the pharmaceutically acceptable salts thereof.

More specifically, this invention is concerned with

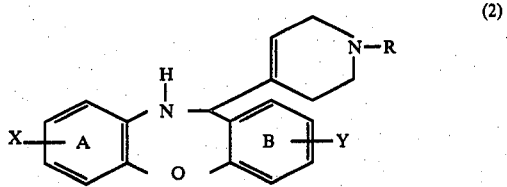

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; R is selected from the group consisting of lower alkyl ($C_1$-$C_6$) and hydroxy lower alkyl; and the pharmaceutically acceptable salts thereof.

DETAILED DESCRIPTION OF THE INVENTION

The compounds of the present invention may be prepared according to the following reaction sequence wherein X, Y, and R are as hereinabove described and Z is chlorine, bromine or iodide.

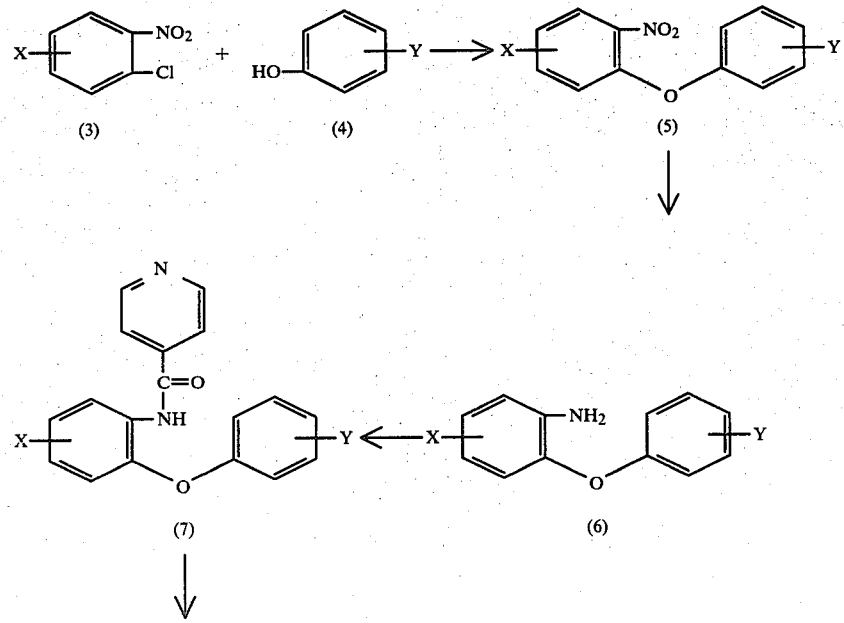

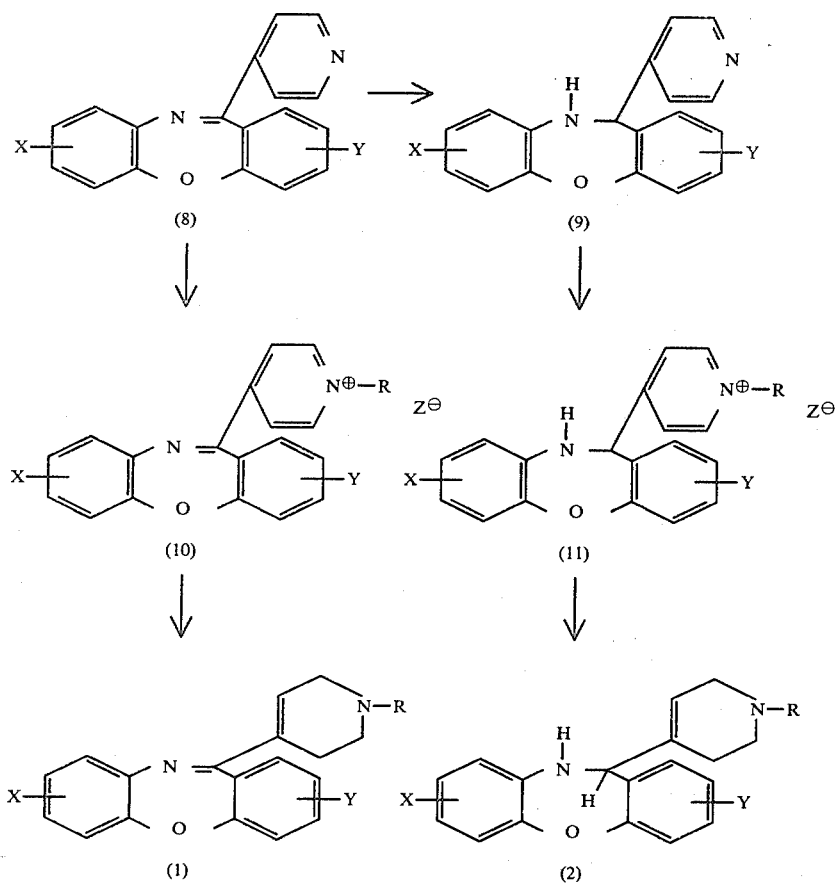

In accordance with this sequence a 1-chloro-2-nitrobenzene (3) is reacted with a phenol (4), a base (such as potassium carbonate) where necessary in a solvent such as benzene or dimethylacetamide with heat giving a 3-nitrophenyl ether (5). This ether (5) is then reduced by conventional means (i.e. sodium hydrosulfite) to the phenoxyaniline (6). Isonicotinic acid is reacted with a mineral acid halide such as thionyl chloride heat or by heating at reflux methylene chloride. The volatiles are evaporated and the residue is reacted with the phenoxyaniline (6) and a base such as triethylamine or potassium carbonate in a solvent such as tetrahydrofuran or benzene at a temperature from 25° to 80° for several hours giving a phenoxy-isonicotinanilide (7). This compound (7) is then reacted with phosphorous pentoxide and phosphorous oxychloride at reflux for several hours. The volatiles are removed at reduced pressure and the residue is reacted with ammonium hydroxide in ice and extracted in methylene chloride giving an 11-(4-pyridyl)-dibenz[b,f][1,4]oxazepine (8). This oxazepine (8) is then reacted with an alkyl halide in a solvent such as acetone or methylene chloride is produce (10) where (R) is as described. This salt is then reacted with sodium borohydride in a solvent such as methanol:water (90:10) or ethanol and extracted with ether giving the desired 11-(1,2,3,6-tetrahydro-4-pyridyl)dibenz[b,f][1,4]oxazepine (1).

To produce the 10,11-dihydro-11-(4-pyridyl)-dibenz[b,f][1,4]oxazepines (2), the compound (8) is reduced with an alkali aluminum hydride in ether or benzene at reflux, quenched with water and extracted with methylene chloride. The compound (9) is converted to the salt (11) and then to the 10,11-dihydro-11-(4-pyridyl)-dibenz[b,f][1,4]oxazepines (2) as described above for compound (8).

Among the compounds contemplated by this invention are the following:

8-Chloro-2-methoxy-11-(1,2,3,6-tetrahydro-1-methyl-4-pyridyl)-dibenz[b,f][1,4]oxazepine 2,8-Dichloro-11-(1,2,3,6-tetrahydro-1-methyl-4-pyridyl)-dibenz[b,f][1,4]oxazepine 8-Chloro-10,11-dihydro-2-methoxy-11-(1,2,3,6-tetrahydro-1-methyl-4-pyridyl)-dibenz[b,f][1,4]oxazepine 2,8-Dichloro-10,11-dihydro-11-(1,2,3,6-tetrahydro-1-methyl-4-pyridyl)-dibenz[b,f][1,4]oxazepine 8-Chloro-11-(1,2,3,6-tetrahydro-11-methyl-4-pyridyl)-dibenz[b,f][1,4]oxazepine 8-Chloro-11-(1,2,3,6-tetrahydro-11-methyl-4-pyridyl)-dibenz[b,f]oxazepine hydrochloride The compounds of the present invention are physiologically active on the central nervous system and show high activity as anti-psychotic agents.

A useful test for anti-psychotic activity consists of measuring the reduction of spontaneous motor activity in animals.

Reduced Locomotor Activity

The use of reduced motor activity as a measure of tranquilizing activity has been described by W. D. Gray, A. C. Osterberg and C. E. Rauh, Arch. Int. de Pharmaco. et de Therapie., 134, 198–215 (1961) and by W. J. Kinnard and C. J. Carr, J. Pharmaco. and Exp.

Ther., 121 354–361 (1957). The test compounds are administered orally to six to 10 individual rats in graded doses. After one hour, a 5 minute count of motor activity is recorded in an activity counter (Animex ®, Farad Electronics, Sweden). A compound is considered active at a given dose if it causes a 50% reduction of the motor activity count when compared to controls. The results of this test on representative compounds of the present invention appear in Table I.

TABLE I

| Compound | Result |
| --- | --- |
| 8-Chloro-2-methoxy-11-(1,2,3,6-tetrahydro-1-methyl-4-pyridyl)-dibenz[b,f]-[1,4]oxazepine | active* |
| 8-Chloro-11-(1,2,3,6-tetrahydro-1-methyl-4-pyridyl)-dibenz[b,f] [1,4]-oxazepine hydrochloride | active* |
| 8-Chloro-11-(1,2,3,6-tetrahydro-1-methyl-4-pyridyl)-dibenz[b,f] [1,4]-oxazepine | active* |

*active = motor activity reduction

Protection versus d-Amphetamine Lethality in Grouped Mice

Known anti-psychotics such as chlorpromazine and haloperidol protect grouped mice from the lethal effects of d-amphetamine sulfate. Other types of "tranquilizers" such as Librium ® and Valium ® are ineffective.

Groups of 10 mice are treated orally with the test compounds at a dose of 5 or 10 mg./kg. of body weight. After periodic absorption times the mice are subsequently given intraperitoneal injections of d-amphetamine sulfate at a dose of 15 mg./kg. The time of peak effect is established as the absorption time for the respective compounds that protect the greatest percentage of mice from death within 24 hours, with $\geq 50\%$ protection being considered active.

The results of typical compounds of this invention appear in Table II.

TABLE II

| Compound | Result |
| --- | --- |
| 8-Chloro-2-methoxy-11-(1,2,3,6-tetrahydro-1-methyl-4-pyridyl)-dibenz[b,f] [1,4]-oxazepine | active* |
| 8-Chloro-11-(1,2,3,6-tetrahydro-1-methyl-4-pyridyl)-dibenz[b,f] [1,4]oxazepine hydrochloride | active* |
| 8-Chloro-11-(1,2,3,6-tetrahydro-1-methyl-4-pyridyl)-dibenz[b,f] [1,4]oxazepine | active* |
| 2,8-Dichloro-10,11-dihydro-11-(1,2,3,6-tetrahydro-1-methyl-4-pyridyl)-dibenz[b,f] [1,4]oxazepine | active* |

*active = motor activity reduction

The active components of this invention can be used in compositions such as tablets. The principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The dosage may vary from 1 mg. to 70 mg. per kg. of warm-blooded animal per day preferably in multiple doses. The daily dosage requirement may be from 50 mg. to 2000 mg. The specification for the novel dosage forms of this invention are indicated by characteristics of the active component and the particular therapeutic effect to be achieved or the limitations inherent in the art of compounding such as active component for therapeutic use in warm-blooded animals as disclosed in this specification. Examples of suitable oral dosage forms in accord with this invention are tablets capsules, pills, powder packets, granules, wafers, cachets, teaspoonsful, droppersful, ampules, vials, segregated multiples of any of the foregoing and other forms as herein described.

The invention will be better understood with reference to the following examples. These examples are intended to be illustrative of the invention which will be limited only by the claims.

EXAMPLE 1

8-Chloro-2-methoxy-11-(1,2,3,6-tetrahydro-1-methyl-4-pyridyl)-dibenz[b,f][1,4]oxazepine To a mixture of 96.0 g. of 1,4-dichloro-2-nitrobenzene, 62.0 g. of 4-methoxy phenol and one liter of benzene is added 80.0 g. of potassium carbonate and 2.0 g. of activated copper. The mixture is stirred and heated on a steam bath overnight, then filtered and the solvent is removed in vacuo yielding 4-methoxyphenyl-4-chloro-2-nitrophenyl ether.

An 80.0 g. portion of the above nitro derivative in 800 ml. of acetone is added to 320.0 g. of sodium hydrosulfite in 800 ml. of water. The mixture is heated to reflux on a steam bath for one hour, cooled and extracted with benzene. The benzene extract is washed with water, dried over anhydrous sodium sulfate, and evaporated in vacuo to a yellow oil. Treatment in hexane, with cooling produces crystals of 5-chloro-2-(p-methoxyphenoxy)-aniline.

A mixture of 19.5 g. of isonicotinic acid, 100 ml. of thionyl chloride and 100 ml. of methylene chloride is heated under reflux for 2 hours. The solvent is evaporated, 200 ml. of benzene is added and this solvent is evaporated. To the residue is added 1200 ml. of benzene, 80.0 g. of anhydrous potassium carbonate and 39.0 g. of 5-chloro-2-(p-methoxyphenoxy)aniline. The mixture is heated under reflux for 8 hours, water is added and the product is extracted in benzene. The benzene extracts are washed, dried and evaporated to a solid residue which is collected with the aid of ether and crystallized from methanol, yielding 5'-chloro-2'-(p-methoxyphenoxy)-isonicotinanilide.

A 40.0 g. portion of the preceding compound is added to 50.0 g. of phosphorous pentoxide and 300 ml. of phosphorous oxychloride. The mixture is stirred and heated under reflux for 20 hours, cooled and swamped with ether. The precipitate is collected, washed with ether and added protionwise, with stirring, to a mixture of 150 ml. of concentrated ammonium hydroxide and ice. This mixture is extracted with methylene chloride. The extracts are washed, dried and evaporated to a residue. The residue is crystallized from acetone, giving 8-chloro-2-methoxy-11-(4-pyridyl)-dibenz[b,f][1,4]oxazepine, mp. 158°–160° C.

A 10 ml. portion of methyl iodide* is added to a solution of 5.0 g. of the preceding compound in 20 ml. of methylene chloride. The mixture is heated under reflux for one hour, ether is added, the precipitate is collected and washed with ether yielding 4-(8-chloro-2-methoxydibenz[b,f][1,4]oxazepin-11-yl)-1-methyl-pyridinium iodide.

*Lower alkyl halides ($C_1$-$C_4$) are also suitable in the methylation steps of this invention.

A 3.5 g. portion of sodium borohydride is added in portions with stirring over 30 minutes to a solution of 3.5 g. of the above methyl iodide derivative in a mixture of 70 ml. of methanol and 7 ml. of water. The mixture is quenched with water and the product is extracted with ether. The extract is washed, dried and evaporated to a residue. The residue is crystallized from methanol yielding the desired product; mp. 146°–148° C.

EXAMPLE 2

2,8-Dichloro-11-(1,2,3,6-tetrahydro-1-methyl-4-pyridyl)-dibenz[b,f][1,4]oxazepine A 152.85 g. portion of p-chlorophenol and 56.1 g. of potassium hydroxide are stirred and heated to 150°–160° C. in an oil bath. When solution is complete the mixture is cooled to 100°–110° C. and 0.5 g. of activated copper powder (prepared by treating copper powder with 5% hydrochloric acid, washing with water, acetone and ether and drying at 100° C. for 15 minutes) is added. A 67.2 g. portion of 1,4-dichloro-2-nitrobenzene is added and the mixture is heated to 170°–180° C. in an oil bath to start the reaction. The oil bath is removed until the reaction subsides, a second 67.2 g. portion of 1,4-dichloro-2-nitrobenzene is added, the mixture is heated to 180° C. for 30–60 minutes, cooled, water is added and the product is extracted in ether. The ether is washed, dried and evaporated yielding an oil which is crystallized from methanol, yielding 4-chlorophenyl-4-chloro-2-nitrophenyl ether.

A 140 g. portion of the above nitro derivative in 1400 ml. of acetone is reduced with 560 g. of sodium hydrosulfite in 1400 ml. of water as described in Example 1, giving 5-chloro-2-(p-chlorophenoxy)aniline.

A mixture of 43.6 g. of isonicotinic acid, 200 ml. of thionyl chloride and 200 ml. of methylene chloride is heated under reflux for 2 hours. The solvent is evaporated, 93.4 g. of 5-chloro-2-(p-chlorophenoxy)aniline, 180.0 g. of anhydrous potassium carbonate and 2800 ml. of benzene are added and the reaction proceeds as described in Example 1. Extraction with petroleum ether gives 5'-chloro-2'-(p-chlorophenoxy)-isonicotinanilide.

A 100 g. portion of the preceding compound is added to 125 g. of phosphorous pentoxide and 750 ml. of phosphorous oxychloride and reacted as described in Example 1. The residue obtained by evaporation of the methylene chloride extracts is 2,8-dichloro-11-(4-pyridyl)-dibenz[b,f][1,4]oxazepine, mp. 214°–215° C.

A 20 ml. portion of methyl iodide is added to a solution of 10.0 g. of the preceding compound in 40 ml. of methylene chloride and reacted as described in Example 1, yielding 4-(2,8-dichlorodibenz[b,f][1,4]oxazepin-11-yl)-1-methylpyridinium iodide.

A 7.0 g. portion of this compound and 7.0 g. of sodium borohydride in 140 ml. of methanol and 14 ml. of water are reacted as described in Example 1. Crystallization from acetone yields the desired product, mp. 166°–167° C.

EXAMPLE 3

8-Chloro-10,11-dihydro-2-methoxy-11-(1,2,3,6-tetrahydro-1-methyl-4-pyridyl)-dibenz[b,f][1,4]oxazepine A 5.0 g. portion of 8-Chloro-2-methoxy-11-(4-pyridyl)-dibenz[b,f][1,4]oxazepine (Example 1) is added to 2.5 g. of lithium aluminum hydride in 200 ml. of ether. The mixture is stirred and heated under reflux for 4 hours. Water is added dropwise to decompose the excess lithium aluminum hydride. The ether is decanted and the residue is extracted with methylene chloride which is then combined with the ether, dried and evaporated. The residue is crystallized from acetone-hexane giving 8-chloro-10,11-dihydro-2-methoxy-11-(4-pyridyl)-dibenz[b,f][1,4]oxazepine, m.p. 186°–188° C.

A 14.5 g. portion of the above compound is reacted with 29 ml. of methyl iodide in 58 ml. of methylene chloride as described in Example 1 giving 4-(8-chloro-10,11-dihydro-2-methoxydibenz[b,f][1,4]oxazepin-11-yl)-1-methylpyridinium iodide.

An 18.0 g. portion of the above compound is reacted with 18.0 g. of sodium borohydride in a mixture of 360 ml. of methanol and 36 ml. of water as described in Example 1. The residue from the ether extraction is crystallized from ethylacetate-hexane yielding the desired product, mp. 115°–117° C.

EXAMPLE 4

2,8-Dichloro-10,11-dihydro-11-(1,2,3,6-tetrahydro-1-methyl-4-pyridyl)-dibenz[b,f][1,4]oxazepine A 20.0 g. portion of 2,8-dichloro-11-(4-pyridyl)-dibenz[b,f][1,4]oxazepine (Example 2), 10.0 g. of lithium aluminum hydride and 800 ml. of ether are reacted as described in Example 3, yielding 2,8-dichloro-10,11-dihydro-11-(4-pyridyl)-dibenz[b,f][1,4]oxazepine, mp. 202°–205° C.

A 12.0 g. portion of the above compound is reacted with 24 ml. of methyl iodide in 48 ml. of methylene chloride as described in Example 1, yielding 4-(2,8-dichloro-10,11-dihydrodibenz[b,f][1,4]oxazepin-11-yl)-1-methylpyridinium iodide.

An 11.0 g. portion of the above compound is reacted with 11.0 g. of sodium borohydride in a mixture of 220 ml. of methanol and 22 ml. of water as described in Example 1. The residue from the ether extraction is crystallized from acetonitrile yielding the desired compound, mp. 147°-150° C.

EXAMPLE 5

8-Chloro-11-(1,2,3,6-tetrahydro-1-methyl-4-pyridyl)-dibenz[b,f][1,4]oxazepine hydrochloride and base A 100 ml. portion of thionyl chloride is added dropwise to 28.0 g. of isonicotinic acid over 30 minutes. After an additional 30 minutes the mixture becomes homogeneous. The volatiles are removed in vacuo, 250 ml. of benzene is added and then removed to leave a residue. This residue is suspended in 300 ml. of dry tetrahydrofuran and a solution of 25.0 g. of 5-chloro-2-phenoxyaniline in 63 ml. of triethylamine is added dropwise over 30 minutes and the mixture is stirred overnight. The mixture is poured into 500 ml. of 1 N-sodium hydroxide. The organic layer is separated. The basic layer is extracted with two 100 ml. portions of ether. The ether extracts and organic layer are combined, washed with 250 ml. of water and then with four 200 ml. portions of 10% hydrochloric acid. The combined acid washings are neutralized with concentrated ammonium hydroxide and extracted with three 250 ml. portions of ether. These ether extracts are dried and evaporated yielding 5'-chloro-2'-phenoxyisonicotinanilide as a brown solid.

A 31.98 g. portion of the above compound is combined with 43 g. of phosphorous pentoxide and 300 ml. of phosphorous oxychloride and heated at reflux overnight. The excess phosphorous oxychloride is removed by distillation and the residue is poured onto a mixture of 100 ml. of concentrated ammonium hydroxide and 500 g. of ice. The mixture is extracted with three 250 ml. portions of methylene chloride. The extracts are dried and evaporated to a yellow solid which is crystallized from chloroform-hexane, yielding 8-chloro-11-(4-pyridyl)-dibenz[b,f][1,4]oxazepine.

A 5.46 g. portion of the previous compound and 19.6 g. of methyl iodide in 100 ml. of acetone are heated at reflux for 30 minutes. An additional one gram of methyl iodide is added and heating is continued for 30 minutes. The mixture is cooled, filtered and the solid is dried, yielding 4-(-8-chlorodibenz[b,f][1,4]oxazepin-11-yl)-1-methylpyridinium iodide as a yellow solid.

A 6.23 g. portion of the above iodide salt is suspended in 150 ml. of ethanol and the mixture is cooled in an ice salt bath. A 0.64 g. portion of sodium borohydride is added in portions over 1 minute and the resulting solution is stirred with ice bath cooling for an additional 30 minutes. The reaction is quenched with one ml. of acetone and diluted with 500 ml. of ether. The ether solution is washed with three 250 ml. portions of water, dried with brine and made acidic with hydrochloric acid. The mixture is cooled and filtered giving a tan solid which is crystallized from acetone-ethanol-dimethylformamide yielding the desired product as the hydrochloride, mp. 213°-215° C. Failure to acidify the above ether solution produces compound as a base mp. 143°-145° C.

Other embodiments of the invention will be obvious to those skilled in the art without departing from the spirit of the invention. The foregoing examples have been only illustrative of the invention.

We claim:
1. A compound selected from those of the formula:

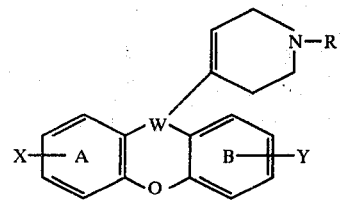

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; R is selected from the group consisting of lower alkyl ($C_1$-$C_6$) and hydroxy lower alkyl; W is selected from the group consisting of

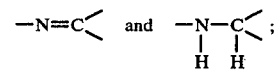

and the pharmaceutically acceptable salts thereof.

2. The compound of claim 1 of the formula:

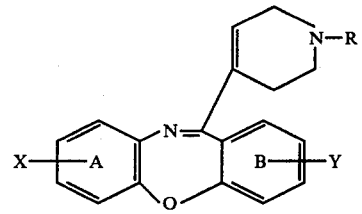

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower) alkylsulfamoyl; R is selected from the group consisting of lower alkyl ($C_1$-$C_6$) and hydroxy lower alkyl; and the pharmaceutically acceptable salts thereof.

3. The compound of claim 1 of the formula:

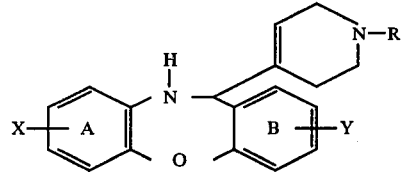

wherein phenyl rings A and B may be unsubstituted, mono-, di- or trisubstituted and X and Y are each selected from the group consisting of hydrogen, halogen, lower alkyl ($C_1$-$C_6$), lower alkoxy ($C_1$-$C_6$), methylthio, trifluoromethyl, nitro, amino and di(lower)alkylsulfamoyl; R is selected from the group consisting of lower alkyl ($C_1$-$C_6$) and hydroxy lower alkyl; and the pharmaceutically acceptable salts thereof.

4. The compound of claim 1, 8-Chloro-2-methoxy-11-(1,2,3,6-tetrahydro-1-methyl-4-pyridyl)-dibenz[b,f][1,-4]oxazepine.

5. The compound of claim 1, 2,8-Dichloro-11-(1,2,3,6-tetrahydro-1-methyl-4-pyridyl)-dibenz[b,f][1,4]oxazepine.

6. The compound of claim 1, 8-Chloro-10,11-dihydro-2-methoxy-11-(1,2,3,6-tetrahydro-1-methyl-4-pyridyl)-dibenz[b,f][1,4]oxazepine.

7. The compound of claim 1, 2,8-Dichloro-10,11-dihydro-(1,2,3,6-tetrahydro-1-methyl-4-pyridyl)-dibenz[b,f][1,4]oxazepine.

8. The compound of claim 1, 8-Chloro-11-(1,2,3,6-tetrahydro-11-methyl-4-pyridyl)-dibenz[b,f][1,4]oxazepine.

* * * * *